United States Patent
Lam (10) Patent No.: US 8,206,434 B2
(45) Date of Patent: Jun. 26, 2012

(54) STENT WITH SINUSOIDAL WAVE FORM AND ORTHOGONAL END AND METHOD FOR MAKING SAME

(75) Inventor: Rui Lam, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 220 days.

(21) Appl. No.: 12/715,675

(22) Filed: Mar. 2, 2010

(65) Prior Publication Data

US 2011/0218614 A1 Sep. 8, 2011

(51) Int. Cl.
*A61F 2/06* (2006.01)
(52) U.S. Cl. ..................................................... 623/1.22
(58) Field of Classification Search .......... 606/1.15–1.2, 606/1.22; 623/1.15–1.2, 1.22
See application file for complete search history.

(56) References Cited

U.S. PATENT DOCUMENTS

| | | |
|---|---|---|
| 2,153,936 A | 4/1939 | Owens et al. |
| 3,185,185 A | 5/1965 | Pfund |
| 4,047,544 A | 9/1977 | Seaborn et al. |
| 4,886,062 A | 12/1989 | Wiktor |
| 5,019,090 A | 5/1991 | Pinchuk |
| 5,092,877 A | 3/1992 | Pinchuk |
| 5,133,732 A | 7/1992 | Wiktor |
| 5,226,913 A | 7/1993 | Pinchuk |
| 5,304,200 A | 4/1994 | Spaulding |
| 5,314,472 A | 5/1994 | Fontaine |
| 5,324,472 A | 6/1994 | Page et al. |
| 5,370,683 A | 12/1994 | Fontaine |
| 5,443,498 A | 8/1995 | Fontaine |
| 5,527,354 A | 6/1996 | Fontaine et al. |
| 5,549,663 A * | 8/1996 | Cottone, Jr. ................. 623/1.22 |
| 5,653,727 A | 8/1997 | Wiktor |
| 5,716,396 A | 2/1998 | Williams, Jr. |
| 5,895,406 A | 4/1999 | Gray et al. |
| 5,902,266 A | 5/1999 | Leone et al. |
| 5,913,897 A | 6/1999 | Corso, Jr. et al. |
| 6,042,597 A | 3/2000 | Kveen et al. |
| 6,117,165 A | 9/2000 | Becker |
| 6,136,023 A | 10/2000 | Boyle |
| 6,190,406 B1 | 2/2001 | Duerig et al. |
| 6,203,569 B1 | 3/2001 | Wijay |
| 6,342,067 B1 | 1/2002 | Mathis et al. |
| 6,355,059 B1 | 3/2002 | Richter et al. |
| 6,423,091 B1 | 7/2002 | Hojeibane |
| 6,432,132 B1 | 8/2002 | Cottone et al. |

(Continued)

FOREIGN PATENT DOCUMENTS

EP 945107 9/1999

(Continued)

*Primary Examiner* — Ryan Severson
*Assistant Examiner* — Katherine M Shi (57) ABSTRACT

A stent includes a wave form that includes a plurality of struts and a plurality of crowns. The wave form is wrapped around a longitudinal axis so as to define a plurality of turns, including a first turn disposed at a first angle and a second turn disposed at a second angle relative to the longitudinal axis. A first connection connects an end of the wave form that started the first turn to an adjacent crown of the wave form that completed the first turn, a second connection connects a first crown of the second turn to an adjacent crown that completed the second turn, and a third connection connects a crown of the first turn to an adjacent crown of the second turn. The wave form is disrupted between the first turn and the second turn.

5 Claims, 6 Drawing Sheets

U.S. PATENT DOCUMENTS

| | | |
|---|---|---|
| 6,447,540 B1 | 9/2002 | Fontaine et al. |
| 6,503,270 B1 | 1/2003 | Richter et al. |
| 6,610,086 B1 | 8/2003 | Kock et al. |
| 6,656,219 B1 | 12/2003 | Wiktor |
| 6,730,117 B1 | 5/2004 | Tseng et al. |
| 6,736,844 B1 | 5/2004 | Glatt et al. |
| 6,878,162 B2 | 4/2005 | Bales et al. |
| 6,923,828 B1 | 8/2005 | Wiktor |
| 6,969,402 B2 | 11/2005 | Bales et al. |
| 7,004,968 B2 | 2/2006 | Lootz et al. |
| 7,108,714 B1 | 9/2006 | Becker |
| 7,169,175 B2 | 1/2007 | Cottone, Jr. et al. |
| 7,329,277 B2 | 2/2008 | Addonizio et al. |
| 2002/0095208 A1 | 7/2002 | Gregorich et al. |
| 2003/0083736 A1 | 5/2003 | Brown et al. |
| 2004/0044401 A1 | 3/2004 | Bales et al. |
| 2004/0143318 A1 | 7/2004 | Tseng et al. |
| 2005/0278017 A1 | 12/2005 | Gregorich |
| 2006/0030934 A1 | 2/2006 | Hogendijk et al. |
| 2006/0079955 A1 | 4/2006 | Brown |
| 2007/0219618 A1 | 9/2007 | Cully et al. |
| 2008/0097580 A1 | 4/2008 | Dave |
| 2008/0097582 A1 | 4/2008 | Shanley et al. |
| 2008/0183273 A1 | 7/2008 | Mesana et al. |
| 2008/0215129 A1 * | 9/2008 | Venturelli et al. ........... 623/1.11 |
| 2008/0288053 A1 | 11/2008 | Addonizio et al. |
| 2008/0289389 A1 | 11/2008 | Fitch et al. |
| 2008/0294241 A1 | 11/2008 | Addonizio et al. |
| 2008/0306583 A1 | 12/2008 | Bashiri et al. |
| 2008/0319529 A1 | 12/2008 | Krivoruchko et al. |
| 2008/0319534 A1 | 12/2008 | Birdsall et al. |
| 2008/0319535 A1 | 12/2008 | Craven et al. |
| 2009/0005848 A1 | 1/2009 | Strauss et al. |
| 2009/0024207 A1 | 1/2009 | Addonizio et al. |
| 2009/036976 A1 | 2/2009 | Beach et al. |

FOREIGN PATENT DOCUMENTS

| | | |
|---|---|---|
| EP | 1155664 | 11/2007 |
| GB | 2281865 | 3/1995 |
| WO | WO2007/095466 | 8/2007 |
| WO | WO2008/028964 | 3/2008 |
| WO | WO2008/100783 | 8/2008 |

* cited by examiner

STENT WITH SINUSOIDAL WAVE FORM AND ORTHOGONAL END AND METHOD FOR MAKING SAME

BACKGROUND OF THE INVENTION

1. Field of the Invention

The present invention is related to a method of manufacturing a stent having a sinusoidal wave form and an orthogonal end relative to a longitudinal axis of the stent, as well as to a stent having a sinusoidal wave form and an end that is orthogonal to the longitudinal axis of the stent.

2. Background of the Invention

A stent is typically a hollow, generally cylindrical device that is deployed in a body lumen from a radially contracted configuration into a radially expanded configuration, which allows it to contact and support a vessel wall. A plastically deformable stent can be implanted during an angioplasty procedure by using a delivery system that includes a balloon catheter bearing a compressed or "crimped" stent, which has been loaded onto the balloon. The stent radially expands as the balloon is inflated, forcing the stent into contact with the body lumen, thereby forming a support for the vessel wall. Deployment is effected after the stent has been introduced percutaneously, transported transluminally, and positioned at a desired location by means of the balloon catheter.

Stents may be formed from wire(s), may be cut from a tube, or may be cut from a sheet of material and then rolled into a tube-like structure. While some stents may include a plurality of connected rings that are substantially parallel to each other and are oriented substantially perpendicular to a longitudinal axis of the stent, others may include a helical coil that is wrapped around the longitudinal axis at a non-perpendicular angle. Helical stents tend to have ends that are not perpendicular to the longitudinal axis due to the pitch of the helix. To square off the ends of a helical stent, the last turn at either end may include a wave form that includes waves of varying amplitudes. However, by varying the amplitudes of the waves, the stent may exhibit non-uniform behavior as the stent is crimped onto a balloon and/or expanded at the deployment site. For example, when the stent is deployed, some of the struts may open more widely than other struts, which may cause uneven vessel support along the inner circumference of the vessel wall.

SUMMARY OF THE INVENTION

It is desirable to provide a helical stent that is configured to contract and expand more uniformly, and to provide more uniform vessel support along the inner circumference of the vessel wall.

It is an aspect of the invention to provide a method of manufacturing a stent. The method includes forming a wave form having a plurality of struts and a plurality of crowns, with each crown connecting two adjacent struts; wrapping the wave form about a longitudinal axis to define a plurality of turns so that a first turn is disposed at a first angle relative to the longitudinal axis, a second turn is disposed at a second angle relative to the longitudinal axis, the second angle being less than the first angle; connecting an end of the wave form that started the first turn to an adjacent crown of the wave form that completed the first turn with a first connection; connecting a first crown of the second turn of the wave form to an adjacent crown that completed the second turn with a second connection; connecting a crown of the first turn of the wave form that is separated from the crown of the wave form that completed the first turn by a single strut to an adjacent crown of the second turn of the wave form with a third connection; and disrupting the wave form between the first turn and the second turn.

It is an aspect of the invention to provide a stent that includes a wave form comprising a plurality of struts and a plurality of crowns. Each crown connects two adjacent struts. The wave form is wrapped around a longitudinal axis so as to define a plurality of turns. A first turn is disposed at a first angle relative to the longitudinal axis, and a second turn being disposed at a second angle relative to the longitudinal axis. The second angle is less than the first angle. A first connection connects an end of the wave form that started the first turn to an adjacent crown of the wave form that completed the first turn. A second connection connects a first crown of the second turn to an adjacent crown that completed the second turn, and a third connection connects a crown of the first turn that is separated from the crown of the wave form that completed the first turn by a single strut to an adjacent crown of the second turn. The wave form is disrupted between the first turn and the second turn.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF EMBODIMENTS OF THE INVENTION

The following detailed description is merely exemplary in nature and is not intended to limit the invention or the application and use of the invention. Furthermore, there is no intention to be bound by any expressed or implied theory presented in the preceding technical field, background, brief summary or the following detailed description.

Figure 1:
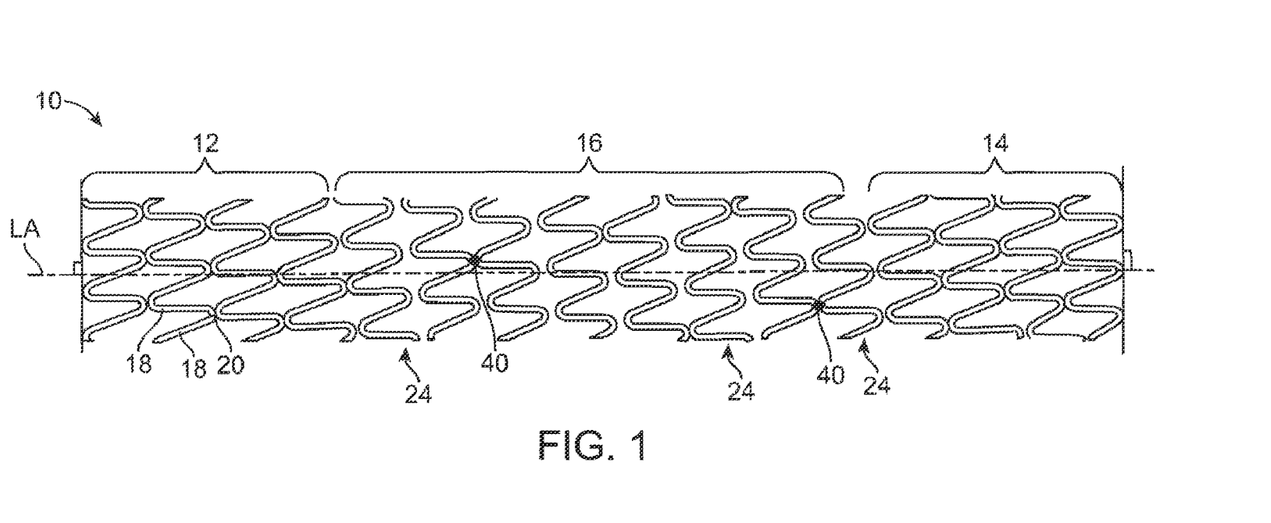
FIG. 1 schematically depicts a stent according to an embodiment of the invention.

FIG. 1 illustrates a stent 10 in an unexpanded configuration according to an embodiment of the invention. As illustrated, the stent 10 has a first end portion 12, a second end portion 14, and a central portion 16 in between the first end portion 12 and the second end portion 14. The first end portion 12 and the second end portion 14 are configured to provide the stent 10 with ends that are orthogonal, or substantially perpendicular to a longitudinal axis LA of the stent 10, which passes through the center of the stent 10, as illustrated in FIG. 1 and discussed in further detail below. In an embodiment, the first end portion 12 and the second end portion 14 may be mirror images of each other. The center portion 16 generally defines a helical coil, as discussed in further detail below.

The stent 10 includes a plurality of struts 18 and a plurality of crowns 20. Each crown 20 is a curved portion or turn that connects adjacent struts 18. As shown in FIG. 1, the struts 18 are substantially straight portions within the stent 10. In other embodiments, the struts 18 may be slightly bent or have other shapes, such as a sinusoidal wave, for example.

Figure 2:
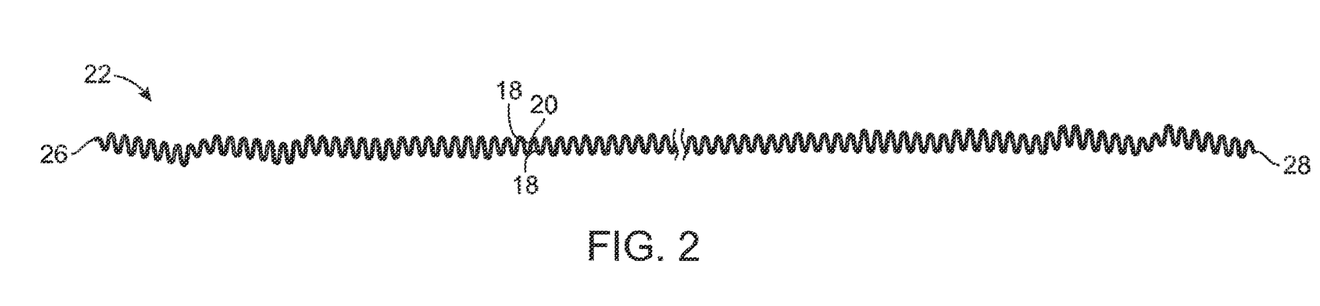
FIG. 2 schematically depicts a wave form used to create the stent of FIG. 1, before the wave form is wrapped around a longitudinal axis to define the stent.

In an embodiment, the stent 10 may be formed from a single wire that has been formed into a generally sinusoidal wave form, such as the wave form 22 illustrated in FIG. 2. The wave form 22 is then wrapped around a mandrel or rod that defines a longitudinal axis that becomes the longitudinal axis LA of the stent 10. The wave form 22 is wrapped around the longitudinal axis LA in a manner that creates a plurality of turns 24, as illustrated in FIG. 1, and discussed in further detail below. As illustrated in FIG. 2, the wave form 22 has a first end 26 and a second end 28 and has a plurality of waves that are defined by the struts 18 and the crowns 20 in between the first and second ends 26, 28.

Figure 3:
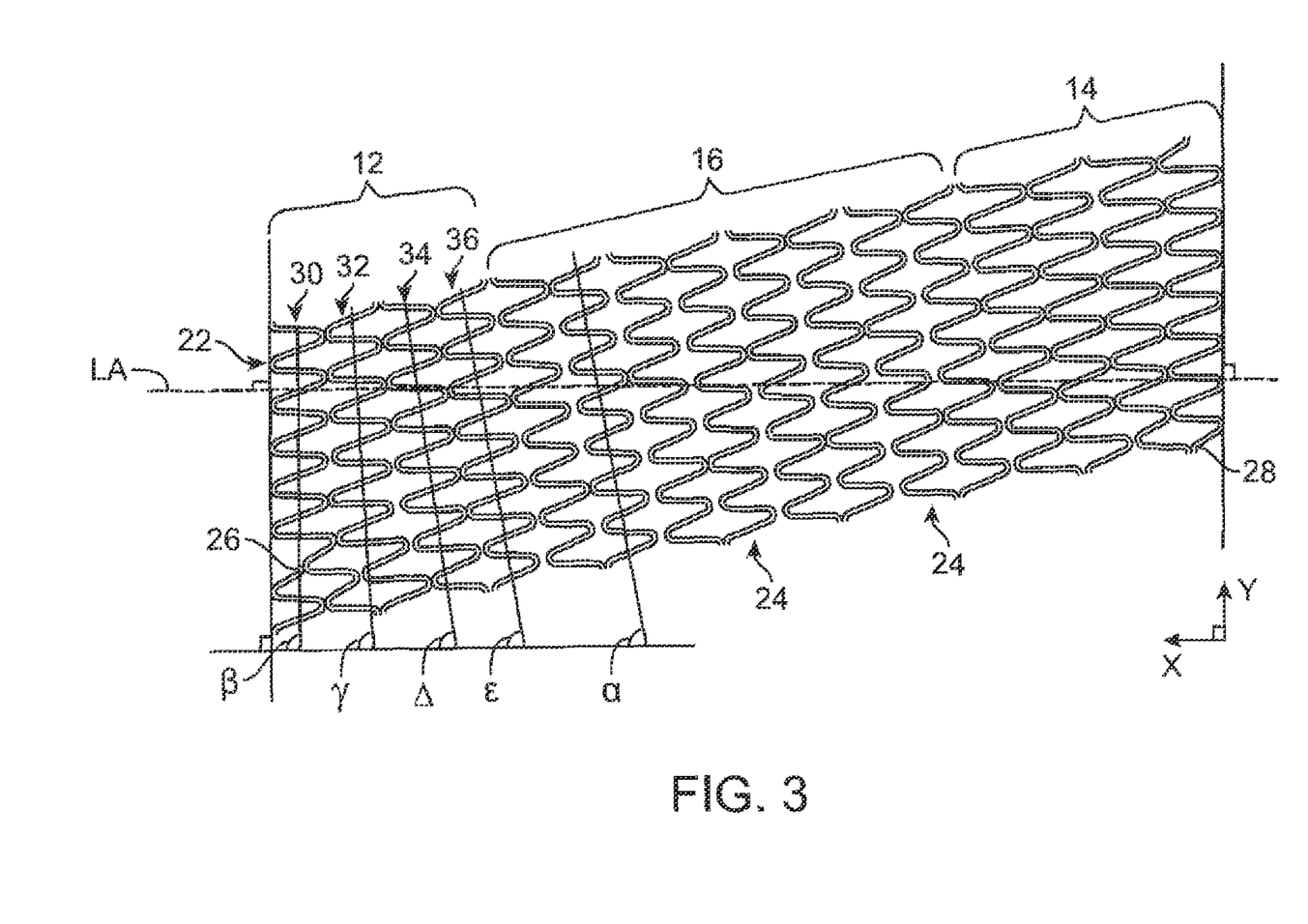
FIG. 3 schematically depicts the wave form of FIG. 2, in an unrolled configuration, after the wave form has been wrapped around the longitudinal axis.

FIG. 3 illustrates the partially formed stent 10 in an "unrolled" state, which may be created when the stent 10 is slit from one end to the other, after the wave form 22 of FIG. 2 has been wrapped around the mandrel or rod. As illustrated in FIG. 3, the wave form 22 is wrapped around the longitudinal axis LA a different pitches so that the wave form 22 generally defines a helical coil in the central portion 16 having a first helical angle, or first pitch angle $\alpha$, and also defines ends that are substantially orthogonal, i.e., square or perpendicular, with respect to the longitudinal axis LA. Specifically, crowns 20 that define the ends of the stent 10 lie in a plane that is substantially perpendicular to the longitudinal axis LA, as illustrated in FIGS. 1 and 3. The first end portion 12 includes a first turn 30 that is wrapped about the longitudinal axis LA at an angle $\beta$ of about 90° so that the stent 10 has an end that is substantially orthogonal or perpendicular to the longitudinal axis LA.

The number of turns 24 about the longitudinal axis and the first helical angle $\alpha$ may be determined by the particular specifications of the stent 10, such as the desired unexpanded and expanded diameters and the length of the stent, as well as the size (e.g., diameter) and particular material of the wire or strip of material that may be used to create the wave form 22. The illustrated embodiment is not intended to be limiting in any way.

The first end portion 12 also includes a second turn 32 that is a continuation of the wave form 22 from the first turn 30. The second turn 32 is wrapped about the longitudinal axis LA at a second pitch angle $\gamma$ that is less than $\beta$ but greater than the first pitch angle $\alpha$. Additional turns may be part of the first end portion 12, such as a third turn 34, and a fourth turn 36, and the additional turns may be configured to provide a more gradual transition between the first turn 30 that is wrapped about the longitudinal axis LA at about 90° and the first pitch angle $\alpha$ of the central portion 16. In the illustrated embodiment, the third turn 34 is wrapped about the longitudinal axis LA at a third pitch angle $\Delta$, which is greater than the first pitch angle $\alpha$ but less than the second pitch angle $\gamma$, and the fourth turn 36 is wrapped about the longitudinal axis LA at a fourth pitch angle $\epsilon$, which is greater than the first pitch angle $\alpha$ but less than the third pitch angle $\Delta$.

In an embodiment, the portion of the wave form 22 that is used to create the first turn 30 has waves that have substantially the same amplitude, i.e., the struts 18 within the first turn 30 have substantially the same length and the crowns 20 within the first turn 30 have substantially the same radius. A strut having a longer length or a shorter length than the remaining struts of the first turn 30 may be used to transition the first turn to the second turn 32. In an embodiment, the lengths of the struts 18 of the first turn 30 may be generally shorter than an average length of the struts of the remaining first end portion 12, i.e., the second, third, and fourth turns 32, 34, 36. In an embodiment, the lengths of the struts of the first turn 30 may be about the same as the lengths of the struts of the central portion 16, which are generally shorter than the average length of all of the struts of the first end portion 12 and of the second end portion 14.

Although the first turn 30 may include struts 18 having substantially the same length, with the exception of the strut that transitions the first turn 30 to the second turn 32, the other turns 32, 34, 36 of the first end portion 12 may include struts 18 having different lengths, with some of the struts 18 having a length that is longer than the average length of all of the struts 18 of the stent 10, and some of the struts having a length that is shorter than the average length of all of the struts 18 of the stent 10. It is desirable to have the length of the longest strut of any given turn to be as short as possible, yet provide the desired transition in pitch angle. The longer struts in the first end portion 12 allow for the transition from the orthogonal end to the helical central portion 16, but may cause the stent 10 to expand unevenly, as compared to central portion 16, when an internal pressure is applied to the stent 10.

Figure 4:
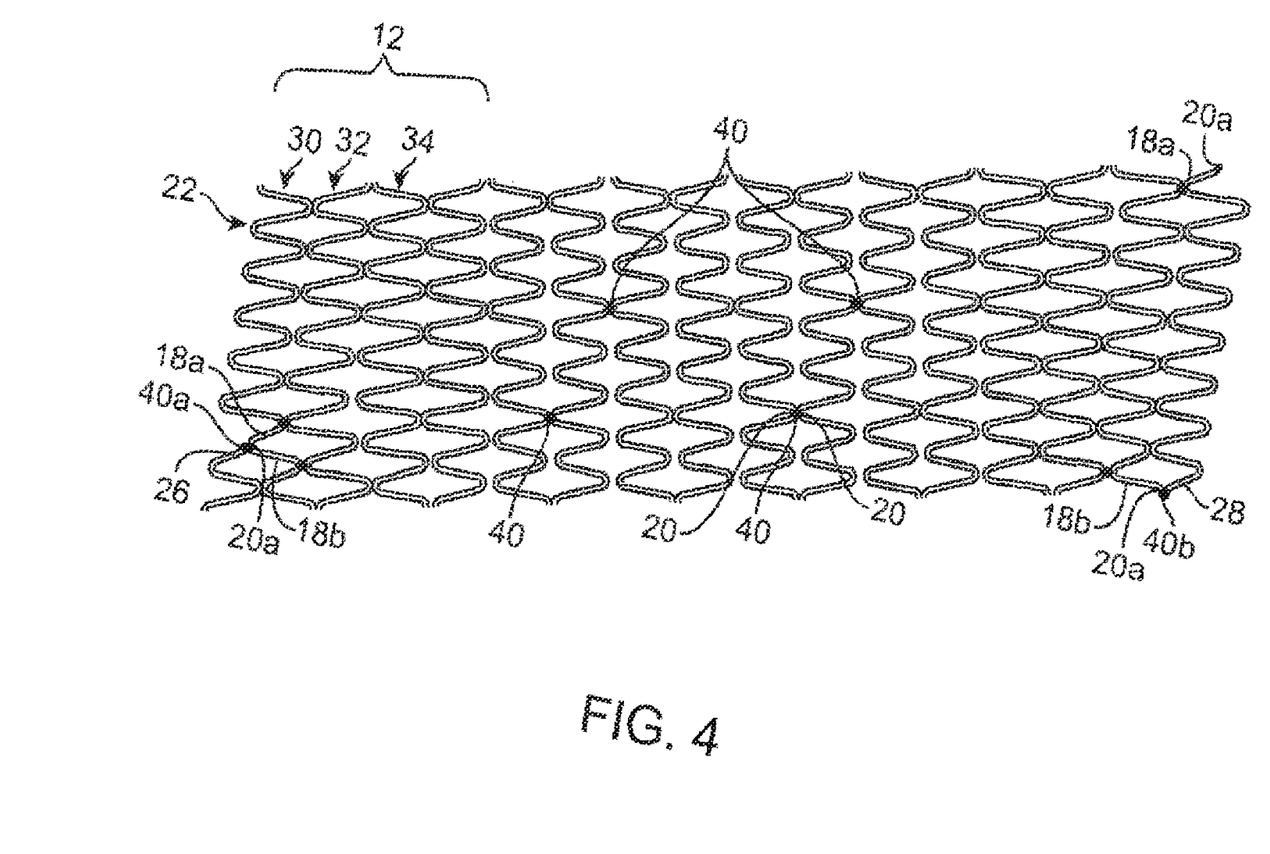
FIG. 4 schematically depicts the wave form of FIG. 3, after connections have been used to connect selected portions of the wave form.

As illustrated in FIG. 4, a plurality of connections 40 are added to the wave form 22 and are configured to connect selected crowns 20 of adjacent turns 24. As illustrated in FIG. 4, a connection 40a is used to connect the first end 26 of the wave form 22 to an adjacent crown 20a, which is the last crown 20 of the first turn 30. Similarly, a connection 40b is used to connect the second end 28 of the wave form 22 to an adjacent crown 20a. Each of the crowns 20a that is connected to one of the ends 26, 28 of the wave form 22 is also directly connected to a pair of struts 18a, 18b.

Figure 5:
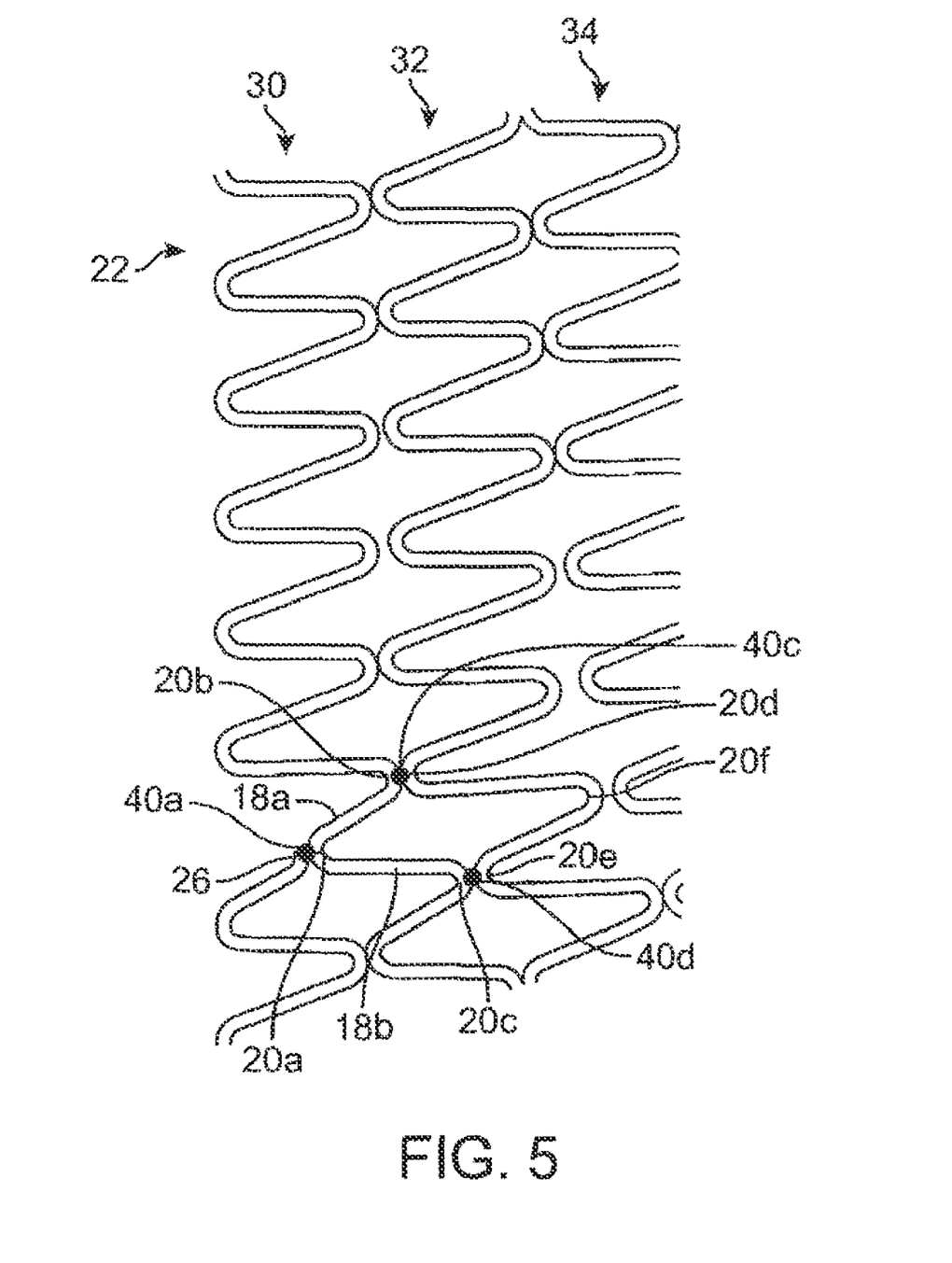
FIG. 5 is a more detailed view of one end of the wave form of FIG. 4.

As illustrated in greater detail in FIG. 5, the strut 18a is connected at one end thereof to the crown 20a and at the other end thereof to another crown 20b. The crown 20b is the next-to-last crown 20 of the portion of the wave form 22 that forms the first turn 30, as the crowns 20a, 20b are only separated by the strut 18a. Similarly, the strut 18b is connected at one end thereof to the crown 20a and at the other end thereof to another crown 20c. The crown 20c is the first full crown of the second turn 32. As illustrated, the crown 20b is connected to an adjacent crown 20d of the second turn 32 via a connection 40c, and the crown 20c is connected to an adjacent crown 20e of the second turn 32 via a connection 40d. The crown 20e may be considered to the last crown 20 of the second turn 32 of the wave form 22. An additional crown 20f is located along the wave form 22 in the second turn 32 in between the crown 20d and the crown 20e, as shown in FIG. 5.

The connections 40 may be created by fusing the selected crowns 20 together. Similarly, the connections 40a, 40b may be created by fusing each end 26, 28 of the wave form 22 to its adjacent crown 20a, respectively, and the connections 40c, 40d may be created by fusing respective crowns 20b and 20d, and 20c and 20e together. As used herein, "fusing" is defined as heating the target portions of the stent 10, e.g., the selected crowns 20, the ends 26, 28, or the adjacent crowns 20a, 20b, 20c, 20d, 20e, to be fused together, without adding any additional material, to a level where the material in the target portions flow together, intermix with one another, and form a fusion when the materials cool down to, for example, room temperature. A suitable laser may be used to create the fusion.

In an embodiment, the connections 40 may be created by welding or soldering the selected crowns 20 together. Similarly, the connections 40a, 40b may be created by welding or soldering each end 26, 28 to its adjacent crown 20a, respectively, and the connections 40c, 40d may be created by welding or soldering respective crowns 20b and 20d, and 20c and 20e together. As used herein, "welding" and "soldering" are defined as heating an additional material that is separate from the portions of the stent 10, e.g., the selected crowns 20, the ends 26, 28, or the adjacent crowns 20a, 20b, 20c, 20d, 20e, to be welded together and applying the heated additional material to the selected portions of the stent 10, so that when the additional material cools, the selected portions of the stent 10 are secured to each other.

In an embodiment, the connections 40, 40a, 40b, 40c, 40d may be created by fusing, welding, or soldering an additional piece of material (not shown) that extends between selected portions of the stent 10 to be connected. The additional piece of material may resemble a strut or a portion of a strut, and may be sized to provide spacing between the selected crowns of two adjacent turns, if desired. The illustrated embodiments are not intended to be limiting in any way.

The size of the connections 40, 40a, 40b, 40c, 40d may also be varied according to the desired flexibility and rate of expansion for a given area of the stent 10. In general, the larger the connection, i.e. the larger the fusion or weld, the greater the stiffness, and the slower the rate of expansion of the stent in the area of the larger connections.

Figure 6:
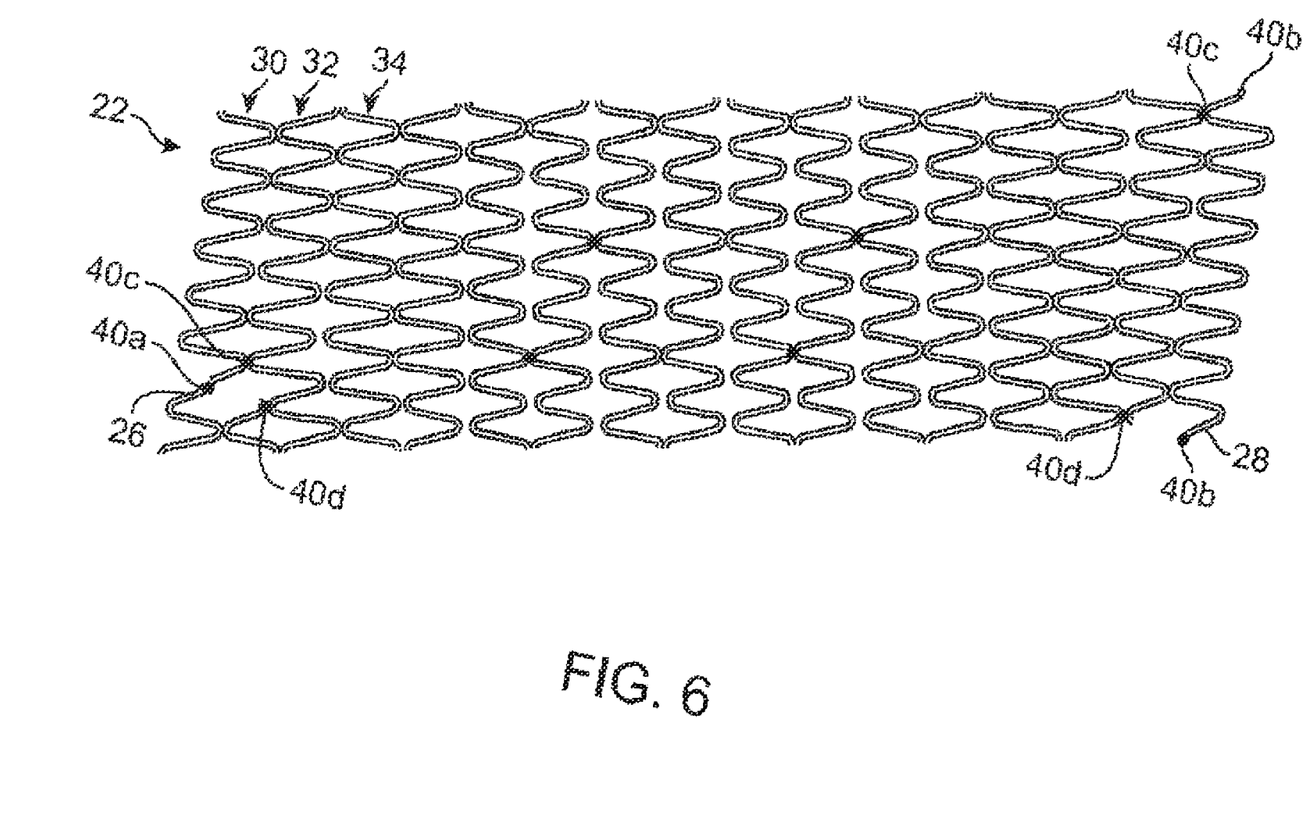
FIG. 6 schematically depicts the wave form of FIG. 4, after a first turn of the wave form has been decoupling from a second turn of the wave form.
Figure 7:
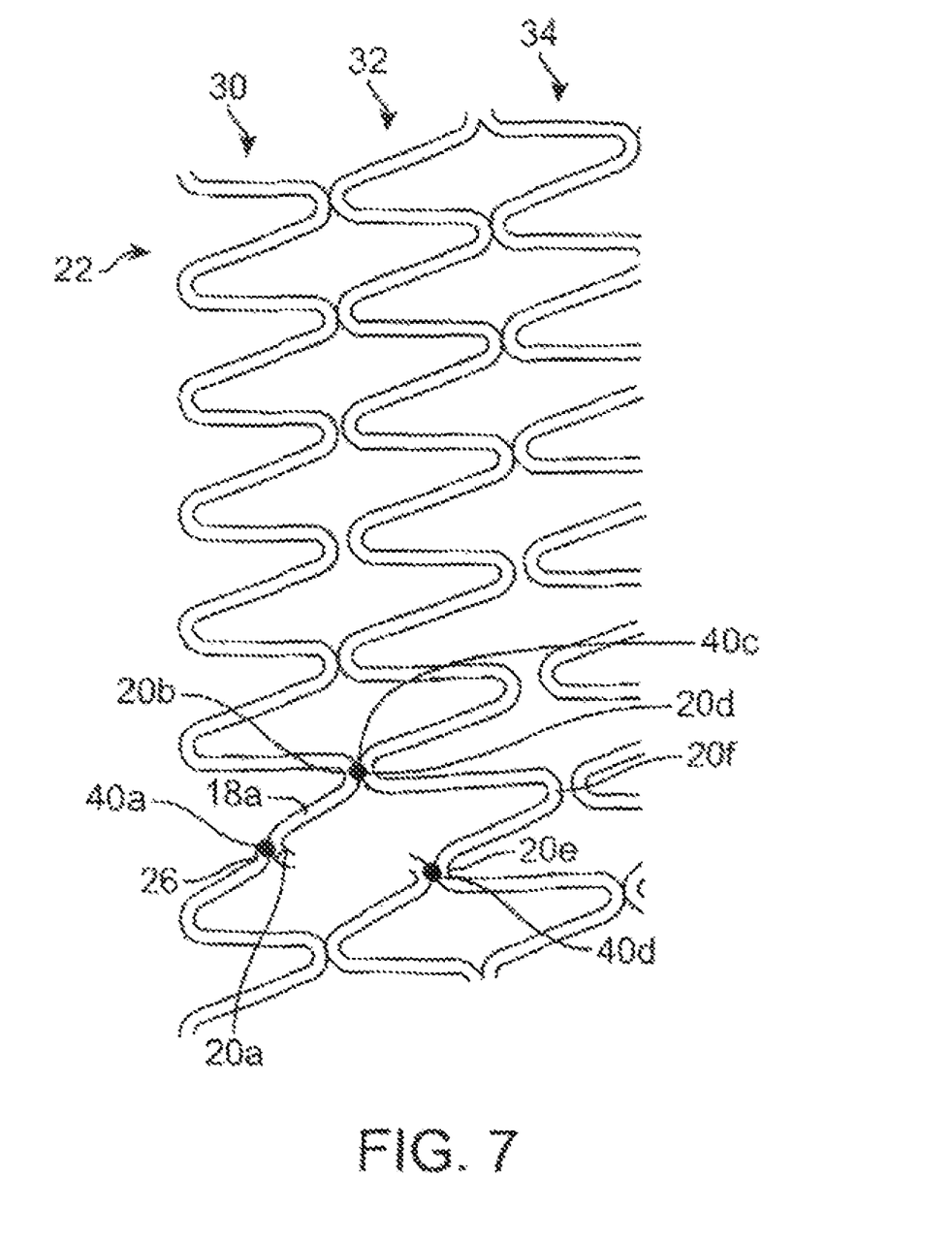
FIG. 7 is a more detailed view of one end of the wave form of FIG. 6.

As illustrated in FIGS. 6 and 7, after the connections 40a, 40c, 40d have been created, the strut 18b may be removed from the wave form 22 to disrupt the wave form 22 so that the wave form 22 is no longer continuous between the first turn 30 and the rest of the wave form 22. By disrupting the wave form 22 at the transition between the first turn 30 and the second turn 32, the first turn 30 may be "decoupled" from the remaining part of the wave form 22 that defines the first end portion 12, as well as the central portion 16, and the second end portion 14. The first turn 30 is still connected to the remaining part of the first end portion 12 with at least two connections 40a, 40c, but the wave form 22 is no longer continuous between the first turn 30 and the second turn 32. As illustrated in FIG. 6, the same strut removal may also occur in the second end portion 14 of the stent 10 to disrupt the wave form 22 and "decouple" the last turn in the stent 10 from the remaining part of the wave form 22 that defines the second end portion 14, as well as the central portion 16, and the first end portion 12. The struts may be removed by using a suitable laser to cut through the struts at opposite ends of the struts.

It has been found that by adding a turn at each end of the stent 10 that includes a portion of the sinusoidal wave form 22 that has a substantially constant amplitude, i.e. the first and last turns of the stent, and by decoupling the first and last turns of the stent from the wave form 22 that defines the remaining first and second end portions 12, 14, respectively, a more uniform deployment may be realized. Although an embodiment of disrupting the wave form 22 between the first turn 30 of the first end portion 12 from the wave form 22 of the remainder of the first end portion 12 is described above as removing a strut 18b from the wave form 22, it is contemplated that other methods to decouple the first turn 30 may be used. The illustrated and above-described embodiment is not intended to be limiting in any way.

The embodiments of the stents discussed above may be formed from a wire or a strip of suitable material. In certain embodiments, the stents may be formed, i.e., etched or cut, from a thin tube of suitable material, or from a thin plate of suitable material and rolled into a tube. Suitable materials for the stent include but are not limited to stainless steel, iridium, platinum, gold, tungsten, tantalum, palladium, silver, niobium, zirconium, aluminum, copper, indium, ruthenium, molybdenum, niobium, tin, cobalt, nickel, zinc, iron, gallium, manganese, chromium, titanium, aluminum, vanadium, and carbon, as well as combinations, alloys, and/or laminations thereof. For example, the stent may be formed from a cobalt alloy, such as L605, super elastic alloys such as MP35N®, Nitinol (nickel-titanium shape memory alloy), ABI (palladium-silver alloy), Elgiloy® (cobalt-chromium-nickel alloy), etc. It is also contemplated that the stent may be formed from two or more materials that are laminated together, such as tantalum that is laminated with MP35N®. The stents may also be formed from wires having concentric layers of different materials. Embodiments of the stent may also be formed from hollow tubes, or tubes that have been filled with other materials. The aforementioned materials and laminations are intended to be examples and are not intended to be limiting in any way.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient roadmap for implementing an exemplary embodiment of the invention, it being understood that various changes may be made in the function and arrangement of members described in an exemplary embodiment without departing from the scope of the invention as set forth in the appended claims.

What is claimed is:

1. A stent comprising:
    a wave form formed from a single wire comprising a plurality of struts and a plurality of crowns, each crown being a curved portion formed between two adjacent struts, the wave form being wrapped around a longitudinal axis so as to define a plurality of turns, a first turn of the wave form at an end of the stent being disposed at a first angle relative to the longitudinal axis, a second turn of the wave form that is a continuation of the first turn being disposed at a second angle relative to the longitudinal axis, the second angle being less than the first angle;
    a first connection between an end of the wave form that starts the first turn and an adjacent crown that completes the first turn;
    a second connection between a first crown of the second turn and an adjacent crown that completes the second turn; and
    a third connection between a next-to-last crown of the first turn and an adjacent crown of the second turn, wherein the next-to-last crown of the first turn is separated by a single strut from the crown that completes the first turn, wherein no strut is located directly between the first connection and the second connection such that the wave form is disrupted between the first turn and the second turn.

2. The stent according to claim 1, wherein the first angle is about 90°.

3. The stent according to claim 1, wherein the struts of the first turn in between a first strut and a last strut are substantially the same length.

4. The stent according to claim 1, wherein the connections are fusions.

5. The stent according to claim 1, wherein the connections are welds.

* * * * *